(12) United States Patent
Trench

(10) Patent No.: US 10,357,785 B2
(45) Date of Patent: Jul. 23, 2019

(54) CENTRIFUGAL SCREENING APPARATUS

(71) Applicant: Weir Minerals Australia Ltd, New South Wales (AU)

(72) Inventor: Michael Trench, Redcliffe (AU)

(73) Assignee: WEIR MINERALS AUSTRALIA LTD., New South Wales (AU)

( * ) Notice: Subject to any disclaimer, the term of this patent is extended or adjusted under 35 U.S.C. 154(b) by 119 days.

(21) Appl. No.: 15/543,824

(22) PCT Filed: Dec. 27, 2015

(86) PCT No.: PCT/AU2015/050848
§ 371 (c)(1),
(2) Date: Jul. 14, 2017

(87) PCT Pub. No.: WO2016/112426
PCT Pub. Date: Jul. 21, 2016

(65) Prior Publication Data
US 2017/0368559 A1   Dec. 28, 2017

(30) Foreign Application Priority Data

Jan. 15, 2015  (AU) .............................. 2015900107

(51) Int. Cl.
*B04B 3/04* (2006.01)
*B04B 7/02* (2006.01)
(Continued)

(52) U.S. Cl.
CPC ................. *B04B 3/04* (2013.01); *B04B 7/02* (2013.01); *B04B 7/12* (2013.01); *B04B 9/08* (2013.01); *B04B 11/02* (2013.01); *B04B 11/04* (2013.01); *B04B 11/06* (2013.01); *B04B 15/00* (2013.01); *G01N 1/20* (2013.01); *G01N 2001/2021* (2013.01)

(58) Field of Classification Search
CPC ...... B01D 33/27; B01D 33/72; B01D 33/763; B04B 3/04; B04B 11/06; B04B 3/00; B04B 5/12
See application file for complete search history.

(56) References Cited

U.S. PATENT DOCUMENTS

| 2,543,599 | A | * | 2/1951 | Rietz | ..................... B02C 13/284 241/185.5 |
| 2,824,703 | A | * | 2/1958 | Van Hook | ............... B02C 13/26 241/193 |

(Continued)

FOREIGN PATENT DOCUMENTS

WO  WO-2014/124926 A1  8/2014

*Primary Examiner* — Ana M Fortuna
(74) *Attorney, Agent, or Firm* — Foley & Lardner LLP

(57) ABSTRACT

In a centrifugal screening apparatus wherein a housing (10, 11) mounts a screen assembly (12) and a scroll assembly (20) to be differentially rotated about the machine axis, there is provided an inlet assembly (30) having an inlet body (31) defining an annular inlet space (32) coaxial with and opening in to an open apical end of the screen assembly (12) and a material supply conduit (35) delivering material to be screened to the annular space (32) and being aligned in a tangent to the annular space to deliver material to the screen assembly (12) substantially in the direction of rotation of the screen assembly (12).

36 Claims, 13 Drawing Sheets

(51) Int. Cl.
*B04B 7/12* (2006.01)
*B04B 11/04* (2006.01)
*B04B 11/02* (2006.01)
*B04B 11/06* (2006.01)
*G01N 1/20* (2006.01)
*B04B 15/00* (2006.01)
*B04B 9/08* (2006.01)

(56) References Cited

U.S. PATENT DOCUMENTS

| | | | |
|---|---|---|---|
| 2,998,137 A * | 8/1961 | Vane | B01D 29/11 |
| | | | 209/17 |
| 3,011,647 A | 12/1961 | Elsken | |
| 5,129,267 A | 7/1992 | Nicholls | |
| 5,380,434 A | 1/1995 | Paschedag | |
| 5,397,471 A | 3/1995 | Rodebush et al. | |
| 5,788,621 A | 8/1998 | Eady | |
| 6,241,190 B1 * | 6/2001 | Lunsford | B64D 1/12 |
| | | | 244/137.3 |
| 6,241,901 B1 | 6/2001 | Leung | |
| 6,514,421 B2 | 2/2003 | Leung et al. | |
| 6,607,473 B2 | 8/2003 | Collier | |
| 6,736,968 B2 | 5/2004 | Mullins et al. | |
| 8,257,587 B2 * | 9/2012 | Angus | B04B 3/04 |
| | | | 210/232 |
| 9,861,915 B2 * | 1/2018 | Trench | B04B 3/00 |
| 2010/0120598 A1 | 5/2010 | Angus et al. | |
| 2016/0325207 A1 | 11/2016 | Trench | |
| 2017/0368558 A1 * | 12/2017 | Trench | G01N 1/20 |
| 2017/0368559 A1 * | 12/2017 | Trench | G01N 1/20 |

* cited by examiner

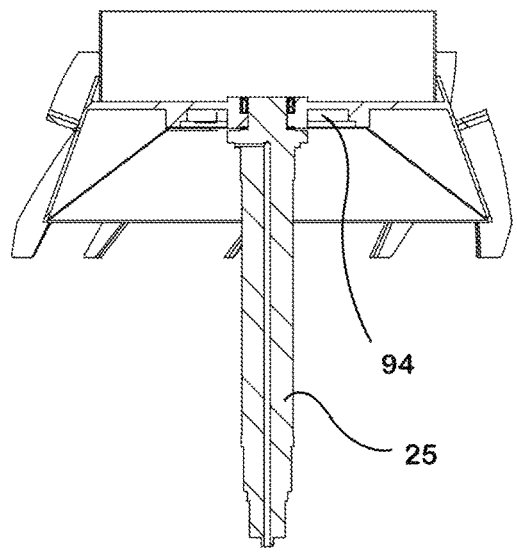
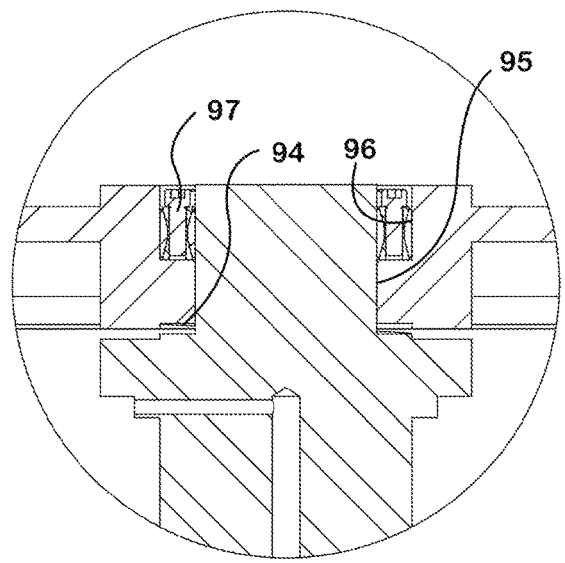
FIG. 7   FIG. 8
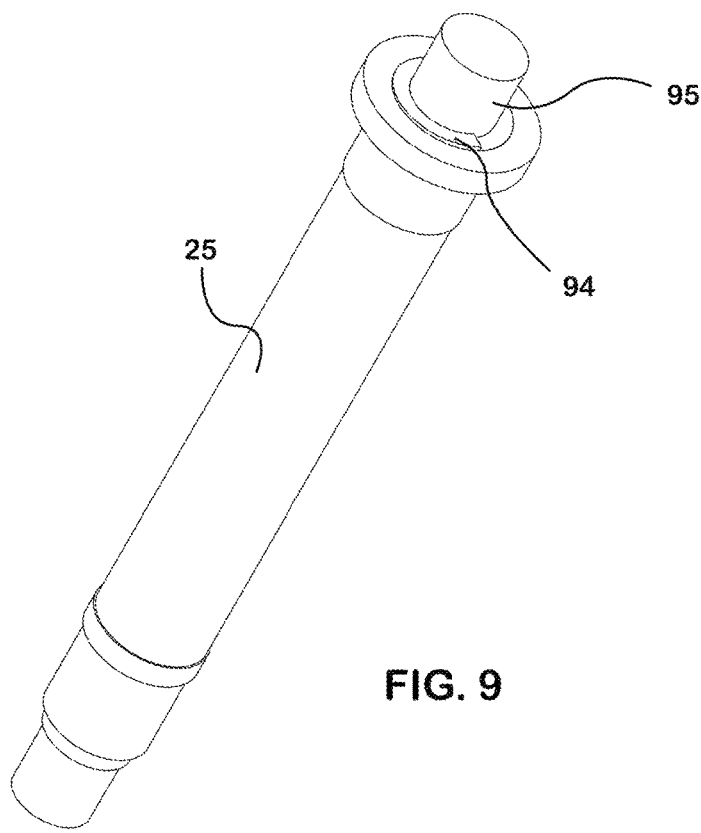
FIG. 9

SECTION A-A

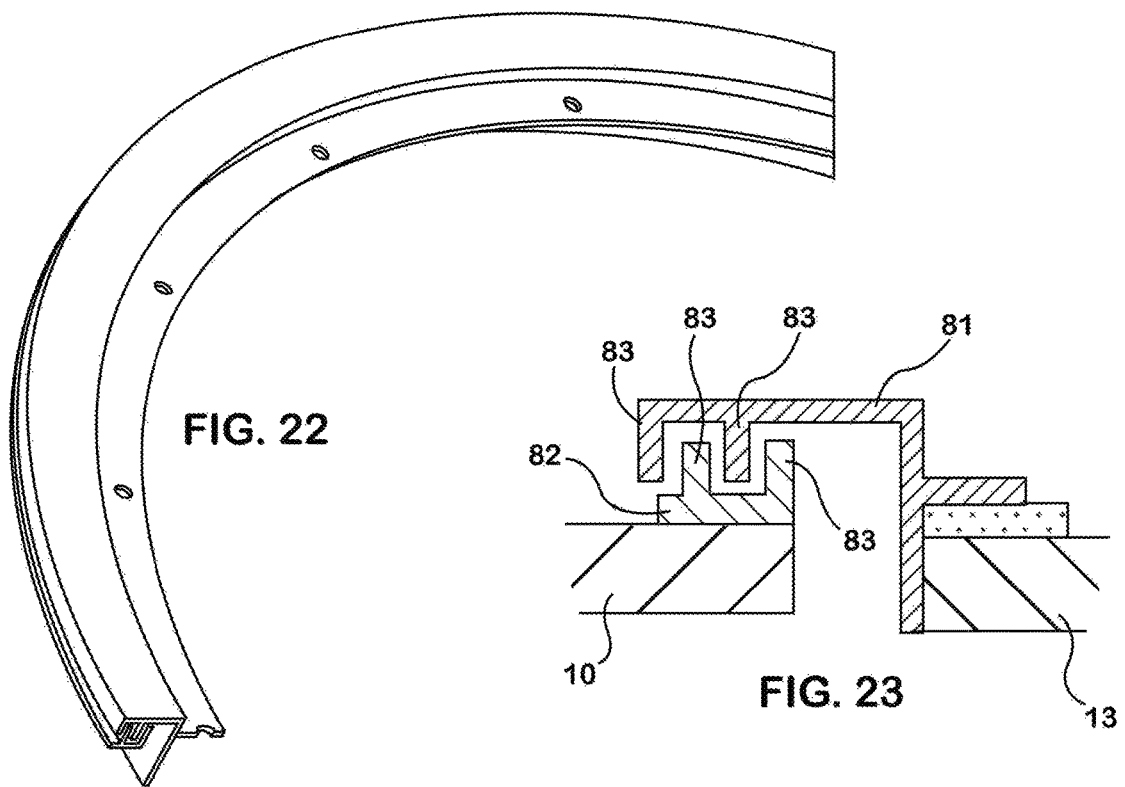
FIG. 22
FIG. 23
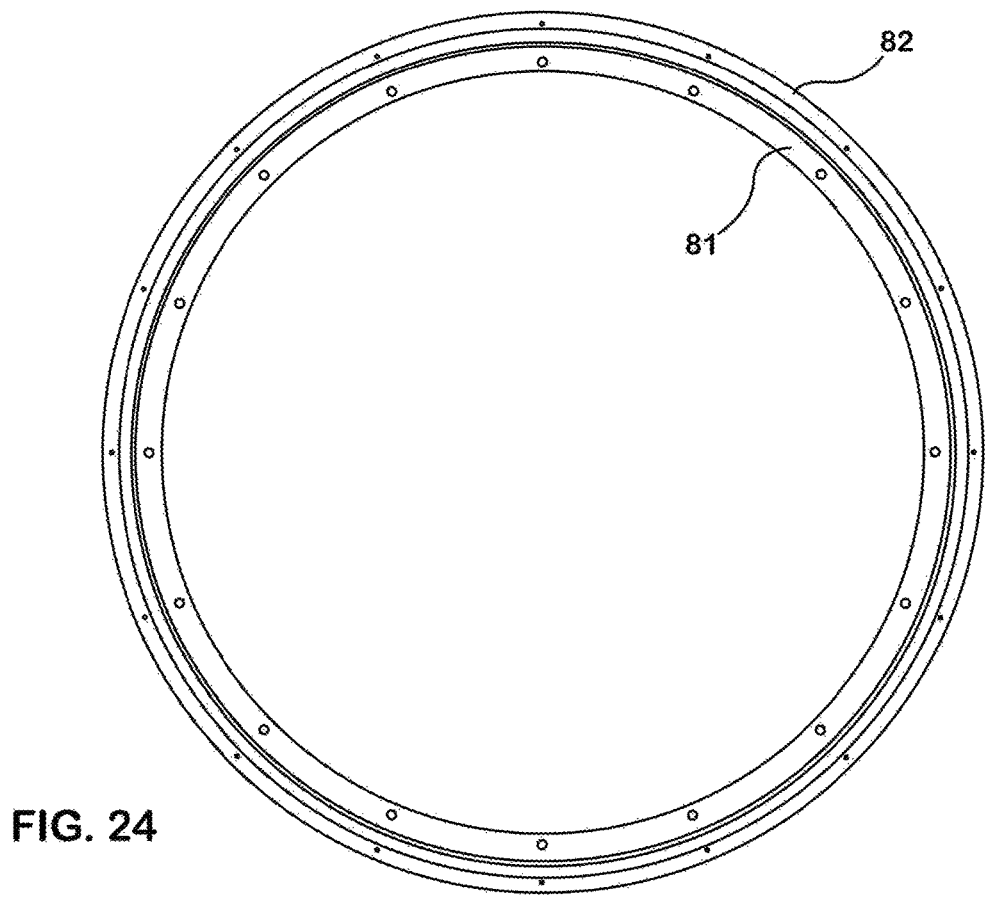
FIG. 24

CENTRIFUGAL SCREENING APPARATUS

CROSS-REFERENCE TO RELATED APPLICATIONS

This application is a United States national phase of international patent application No. PCT/AU2015/050848, filed Dec. 27, 2015, which claims priority to Australian patent application No. 2015900107, filed Jan. 15, 2015, the entire disclosures of which are hereby incorporated herein by reference.

TECHNICAL FIELD

This disclosure relates in general to centrifugal screening apparatus and, in particular, to an improved fine coal centrifugal scroll screen machine.

BACKGROUND OF THE DISCLOSURE

Pulverized coal is washed by forming a water slurry and dewatering the slurry by passage through a fine coal centrifugal scroll screen machine. A typical machine is known as a vertical fine coal centrifugal scroll screen machine and includes a housing, a screen assembly mounted for rotation on a vertical axis in the housing and comprising a base-of-spoke piece supporting the lower, wider end of a frustoconical screen member, the base of spoke piece cooperating with a dividing wall in the housing to form housing portions receiving filtrate passing through the screen member and product passing through the base-of-spoke piece respectively.

The screened coal product is actively stripped from the screening surface of the screen member by a scroll assembly of helical scroll vanes mounted for differential rotation within the screen member, the edges of which scrape the deposited fine coal and urge it through apertures in the base-of-spoke piece. A drive assembly generally comprising an electric motor and gearbox differentially drives the rotation of the screen assembly and scroll assembly mounted on concentric drive shafts. Incoming fine coal slurry passes down vertically under a gravity head into an inlet assembly supported on said housing and feeding in to the upper, narrow end of the screen member.

The commercially important features of a fine coal centrifuge are throughput, ease of maintenance and reduction of downtime. Prior art fine coal centrifuges may require choking or tuning of the gravity head, limiting throughput.

SUMMARY

In a first aspect, the present invention resides broadly in a centrifugal screening apparatus including:
 a housing;
 a screen assembly mounted for rotation in said housing and including a base-of-spoke piece and a substantially frustoconical screen member having an inner screening surface and removably secured by its base to the base-of-spoke piece, the base of spoke piece cooperating with the housing to substantially divide the housing into housing portions receiving filtrate passing through the screen member and product passing through the base-of-spoke piece respectively;
 a scroll assembly having a plurality of substantially helical scroll vanes and mounted for rotation within said screen member with an edge of each said vane lying in selected proximity to said screening surface;
 drive means selected to differentially drive the rotation of said screen assembly and said scroll assembly about a machine axis; and
 an inlet assembly supported on said housing and including an inlet body defining a substantially annular inlet space substantially coaxial with and opening in to an open apical end of said screen member and a material supply conduit delivering said material to be screened to said annular space, said material supply conduit being aligned in a tangent to said annular space selected to deliver said material to said screening surface substantially in the direction of rotation of the screen assembly.

Apparatus having the foregoing features has an advantage over prior art scroll centrifuge machines in that the material supply conduit being aligned in a tangent to the annular space rotates the incoming material substantially in the direction of rotation of the screen assembly. The material needs less acceleration by the screen to reach centrifugally effective speeds, increasing throughput and reducing screen wear. The annular space effectively confines the feed to adjacent the screen surface. This permits the use of product supply gravity head in a substantially self-regulating manner, generally not requiring choke regulation of supply by velocity arrestors or the like. The present invention is readily adapted to a horizontal machine with a vertical gravity feed finding a ready tangent to the horizontal machine axis, with additional advantages accruing as described hereinafter.

In certain embodiments, the inlet assembly may include an inlet body forming the annular inlet space and including an integral spigot to the supply conduit. The inlet space and spigot may be lined with a wear resistant material. The wear resistant material may for example be selected from refractory materials such as sintered ceramic materials and fired ceramic materials.

In certain embodiments, the inlet body may be selected from fabricated or cast metal, moulded engineering polymer and composites. Simpler forms may be readily fabricated from steel. More complex inlet body shapes may be formed by molding as described hereinafter.

In certain other embodiments, the wear resistant lining may selected from wear resistant elements bonded into the inlet body to form the lining and a wear resistant ceramic liner about which the inlet body is formed. The wear resistant elements may be sintered ceramic tiles. For example, the tiles may comprise sintered alumina, other refractory metal oxides or sintered carbides.

In certain other embodiments, the wear resistant lining may be an integral hot sintered ceramic liner having a spigot portion merging with a substantially involute annular inlet space portion. The inlet body may be formed thereabout by molding or, for example, an engineering polymer or composite material.

The wear resistant lining including an involute annular inlet space portion may be produced by, for example, repetitively dipping a wax plug into ceramic powder slurry and drying between dips, to form a green liner. The green liner may be further dehydrated and the wax plug removed by heating, followed by calcining to form a hard ceramic material.

The inlet axis may be inclined to the machine axis. In certain embodiments, the axis of the tangential material supply conduit may lie in a plane that intersects the machine axis by an angle of from 0° to about 10° from the perpendicular, measured away from the screen assembly.

In certain embodiments, the material to be screened may be delivered to the annular inlet space by pressure head means selected from gravity and pump. For example, the head may be provided by the usual gravity head commonly used to supply conventional vertical fine coal centrifuges of the prior art. In most applications, the gravity feed may be supplied without the use of velocity arrestors. In the case of pump feeds, this may include a pump which either replaces or supplements a gravity head. The pump make be selected from all classes of pumps known in the art for moving the particular slurry be screened. For example the pump may be selected from centrifugal pumps.

In certain embodiments, the machine axis may be substantially horizontal. This has several advantages. The use of a horizontal machine with an inlet assembly according to the above does not suffer from the disadvantage of the few prior art horizontal machines of the feed extending the floor plan, since the feed in the present apparatus is tangential to the inlet and machine axis.

The inlet assembly of a horizontal machine may be formed separately from and be hinged to the housing. The inlet assembly may extend its annulus forming outer cylindrical wall into the housing to confine the feed to the annular space defined by the screening surface and the scroll vanes. The portion of the annulus forming outer cylindrical wall extending into the housing may include part of the housing or may include an integral part of the hinged inlet assembly.

Where the portion of the annulus forming outer cylindrical wall extending into the housing includes an integral part of the hinged inlet assembly, the hinge arrangement may be positioned and configured to allow the inlet assembly, including the wall extending into the housing, to clear an aperture in the housing to enable maintenance access. When the inlet assembly is in its closed up position in the housing, there may be provided a gasket arrangement. The gasket arrangement may be compressed by any suitable means. For example the inlet assembly may be secured in the closed position with closure bolts.

In certain embodiments, the housing portions may include a fixed inner portion associated with the drive means and a moveable outer portion associated with the inlet assembly, said inner and outer portions having complementary peripheral mating flanges secured with selectively releasable fixing means. The housing portions may be selectively separable substantially in the plane of a join between the base-of-spoke piece and the screen member. By this means the join is accessible for maintenance when the housing portions are separated.

In certain embodiments, the selectively releasable fixing means may include a plurality of circumferentially spaced key slots associated with the peripheral mating flange of the inner portion and each supporting a blind stud, corresponding stud holes associated with the peripheral mating flange of the outer portion, and securing means selected to engage the studs to clamp said peripheral mating flanges together. Typically the studs and securing means are complementary threaded components.

In certain embodiments, the key slots are formed in slot bodies welded outward of the peripheral mating flange of the inner portion, each slot body and blind stud being retained in assembly by a resilient retainer adapted to pass over the stud and substantially encapsulate the slot body. By this means the blind stud is retained to the housing inner portion by means that protects the arrangement from the aggressive erosive and corrosive environment. This provides an inexpensive and easily replaceable fixing system that addresses both wear and corrosion problems of alternative fixing methods. The welded slot bodies may be formed of stainless steel.

The resilient retainer may comprise a cap having a cylindrical side wall adapted to engage the slot body and substantially closed at one end by an end wall having an aperture adapted to pass over and engage the stud. The resilient retainer may be secured in position by any suitable means. For example, the resilient retainer may be threaded on one or both of the inner cylindrical side wall to engage a complementary threaded side surface of the slot body. The end wall aperture may be internally threaded to engage the corresponding threaded stud. Alternatively, the resilient retainer may be a tight fit on the stud and have a complementary profile to the slot body whereby the retainer may resiliently snap onto the slot body. The resilient retainer may suitably be moulded of a chemically and abrasion resistant elastomeric material such as polyurethane elastomer.

In its simplest embodiment the blind stud includes a bolt and the securing means includes corresponding nut. The bolt and nut are preferably of stainless steel or a like resistant alloy such as MONEL®.

In certain embodiments, the housing portions may relatively conjoined by one or more hinge portions. This is especially the case where the machine orientation is horizontal, where a vertically hinged outer housing portion provides access for ground-level maintenance. The selected configuration of the hinge portions may be geometrically selected to cooperate with a hinged inlet assembly as described above to allow the assembly of the outer housing portion and inlet assembly to be opened with ample clearance of the wet-end parts, to provide maintenance access to the entire wet side of the apparatus. This access is achievable without the use of cranes, in the case of horizontal machines at least.

In the aggressive environment anticipated for screen machines, the hinge portion or portions may be lubricated by a positive pressure lubricator. For example, the positive pressure lubricator may include a grease reservoir pressurized by a spring loaded piston and having a delivery outlet spigot screwed into the bore of a hinge to lubricate the pin-to-bore surfaces thereof. Positive grease pressure resists the ingress of abrasive fines, thus prolonging the service life of the hinge portion.

In certain embodiments, a filtrate or effluent outlet may be integrally formed with the outer housing portion.

In certain embodiments, at least the housing portion receiving filtrate passing through the screen member may be formed of moulded polymer or polymer composite. As the effluent chamber and the wet end of the housing per se is exposed to an abrasive environment in use, an integral outer housing and effluent chamber may be unitarily formed on an engineering polymer material such as ultra-high molecular weight polyethylene (UHMWPE). Alternatively the outer housing may be formed more conventional such as of wear resistance-lined steel, and having attached thereto a polymer or composite effluent chamber portion.

In certain embodiments, the drive means may include a motor and a power-dividing gearbox providing the differential drive through concentric shafts as per the prior art, wherein the gearbox may have a pressurized-circulation lubrication system including at least one lubricant pump delivering lubricant from a reservoir and at least two filters in parallel, each being associated with isolation valve means selected to allow filter maintenance without shut-down of the gearbox.

A conventional gear or other positive-displacement lubrication pump may pressure-supply the gearbox with lubricant from an atmospheric reservoir. Circulated lubricant may be returned to the reservoir via a low pressure return line. The parallel filters may be located in either the supply line or the return line. The filters may be selected from single use or serviceable filter assemblies. For example, each filter may be a disposable spin-on filter cartridge.

The isolation valve means may take any suitable form including, but not limited to electrically selected or manually operated isolation valve means. The respective isolation functions may be integrated into a single action changeover valve and non-return valves. For example, the filters may be supplied by an inlet line from pump by a filter-selecting Y-valve, each filter having a respective non-return valve on its delivery line.

In certain embodiments, the issue of reducing cross contamination of the product and effluent or filtrate streams may be specifically addressed. The rotating base of spoke piece may cooperate with the static housing via a labyrinth selected to substantially resist filtrate contamination of said product. The labyrinth may include respective cooperating labyrinth portions support on a respective one of the base of spoke piece and a housing portion surrounding its periphery. Typical passive labyrinth portions have cooperating pairs of closely-running annular ridges interleaved to create a labyrinth. The labyrinth may be pressurized via a manifold associated with the housing. The manifold may comprise an annular passage formed on the housing portion surrounding the periphery of the base of spoke piece and feeding a pressurized fluid into the labyrinth. The pressurized fluid may be air, since air is not a contaminant for either product or effluent streams.

The respective labyrinth portions, or any one or the other of them, may take the form of a labyrinth portion member as a replaceable service item which operates in a high-wear region.

As an alternative to or in addition to a labyrinth, cross contamination may be addressed by the rotating base of spoke piece cooperates with the static housing by means of a slinger portion associated with the base of spoke piece and selected to substantially resist filtrate contamination of said product. The slinger portion may include an axially directed annular wall secured to the base of spoke piece and adapted to run in proximity to the aperture between the housing portions receiving filtrate passing through the screen member and product passing through the base-of-spoke piece respectively, and a plurality of circumferentially spaced slinger vanes inclined to the machine axis and located radially outward of and adjacent to the annular wall.

In certain embodiments, the slinger portion may include a slinger member including the annular wall and slinger vanes formed on a mounting flange adapted to be secured to the base of spoke piece. The slinger member is thus a replaceable service item which operates in a high-wear region, and additionally serves to protect that portion of the base-of-spoke piece in a sacrificial manner.

The prior art of scroll machines includes methods of adjustment of the clearance between the scroll vane edges and the screening surface to account for running in and relative wear. In every case of disassembly and reassembly the clearance between these items is necessary to fine tune for efficiency. Excess clearance results in material pick up in the machine.

In the past, adjustment of the clearance has required removal of the outer housing portion, attempting to measure the actual clearance by generally-obstructed visual means, estimating the adjustment required, removal of the screening member by crane from the base-of-spoke piece, releasing of the scroll from the shaft by removal of its pattern of bolts while supporting by crane, insertion or removal of a calculated thickness of shim, and reassembling.

In certain embodiments of the present apparatus, the drive means may include the respective concentric drive shaft portions extending axially substantially through the screen assembly, wherein the scroll assembly drive shaft may be connected to the scroll assembly by an axial adjuster operable to adjust the selected proximity. The axial adjuster may include a shaft portion and a scroll portion each having a respective camming surface whereby relative rotation of the scroll portion and the shaft portion axially adjusts the selected proximity, and locking means selectively operable to rotationally secure the scroll portion and the shaft portion.

The locking means may include splines, axially directed locating pins or the like. The locking means is preferably selected to resist malfunction or jamming through the ingress of fines. In any case the axial adjuster is preferably protected in use by a cover such as a polymer cap. For example, the mechanism of the axial adjuster may be protected by a polyurethane elastomer cap.

The locking means may comprise a multi-pin staking device and axial bolt and plate. Such an arrangement provides stepwise adjustment. However, stepless adjustment may be achieved by an expanding coupling between the shaft and the scroll such as that provided by a RINGFEDER® locking means. A scalar indication of adjustment may be provided by inscribed scale marks on outer end faces of the scroll portion and the shaft portion.

In use the hinged inlet assembly only (if used) or the housing outer portion is removed or swung away (in a horizontal embodiment) whereupon the axial adjuster may be exposed. Without removing the screen member and the scroll member (as required by the prior art) the locking means may be released and the scroll member rotated on the shaft to effect adjustment of the clearance between the scroll vanes and the screening surface of the screen member. Thereafter the locking means may be engaged, the protection installed and the housing portions closed together. The initial condition need not be measured at all; the adjustment is dynamic in that the parts are in situ while the adjustment is made. The adjustment can be measured in real time or the clearance fully closed up by one direction of relative rotation of the scroll on the shaft rotation and backed off to create a selected working clearance.

One or both of the shaft portion and the scroll portion may include a replaceable service part secured to its respective shaft or scroll.

In certain embodiments, the fixed inner portion may support a hoist assembly selected to enable maintenance removal and replacement of the wet side components of the apparatus, such as one or more of the scroll assembly and the screen assembly. Where the machine axis is substantially horizontal, the hoist assembly may include a rail supported by the fixed inner housing portion and extending overhead of the outer portion, a hoist mounted for movement along the rail, and hoist adapters connecting a lifting terminus of the hoist to one or more of the scroll assembly and the screen assembly.

The rail may comprise a monorail extending far enough to deliver components to a trolley, with may be customized to receive a components in its in-use orientation. The hoist may be a cable hoist or a chain hoist. The hoist adapters may be generic hooks or grabs. It is preferred that the hoist adapters be custom configured to lift each component substantially though its centre of gravity.

Whereas the prior art requires an external crane, certain embodiments herein are capable of change out of components without additional overhead lifting gear. Whereas prior art overhead lifting gear is generally multipurpose and must be rated accordingly, the present embodiments are rating matched to the actual machine components. The relative short cable or chain length to the component reduces the risk of load swing.

The scroll assembly includes structure to support the scroll vanes relative to the scroll drive shaft. To a greater or lesser extent, the geometry of scroll members of the prior art has tended to allow hang-up of product internally of the scroll member, which can lead to increasing rotating mass and out-of-balance operation. In certain embodiments, the present scroll assembly includes a substantially frustoconical liner substantially interconnecting inner edges of the vanes and spaced from the screening surface, said liner extending substantially to the base-of-spoke piece. The scroll vanes may be rendered more wear resistant than the base metal by laminating the metal faces with adhesively bonded ceramic elements.

The liner may also extend substantially to the outer ends of the vanes. The liner may be integrated into a collar portion that cooperates with the inlet assembly to confine the infeed of material to the annulus containing the vanes.

In the event that the conical included angle of the liner is such that product hang-up still occurs, the liner may be associated with an inner conical wall portion creating an enclosed annulus within the liner and presenting a flatter conical included angle. By this means any material passing into the space is discouraged from hanging up since the centrifugal component of the forces acting through the flatter conical surface will direct the product toward the base-of-spoke piece.

Sampling of product quality is an important control element. The existing inspection doors on centrifuges (which in previous days were used to take samples) comprises a manual unrestrained sampling scoop inserted into a moving stream with rotating parts nearby. It is desirable that a sampler should have repeatability so that the sample should be consistent enough to see small changes in product output moistures.

A centrifugal scroll screen machine according to the foregoing description may include a product sampler. For example, a product sampler may comprise a tubular body mounted by a first open end to a corresponding aperture though a wall of the product housing portion, the tubular body having its tubular axis substantially perpendicular to a product flow in said housing portion. A sample shuttle may comprise a tubular receptacle selectively and captively movable in the tubular body between a sampling position where a sampling portion extends into the product flow and a sample delivery position with a delivery portion extended out of a second open end of the tubular body, the sampling portion having side wall opening which faces substantially upstream of the product flow and the delivery portion having a delivery opening. A piston assembly may be captively slidable in the sample shuttle and may have a piston portion and a control rod portion extending out of the second open end, the rod portion being operable to selectively move the piston portion from a position located adjacent a terminal end of the sampling portion to a position adjacent an outer end of the delivery opening.

The sampler may have a tubular body and sample shuttle which are each substantially cylindrical in section.

The sample shuttle may be made captively moveable in the tubular body by an operating handle attached to the sample shuttle extending out of and movable along an axial slot formed in the cylindrical side wall portion of the tubular body.

Other aspects, features, and advantages will become apparent from the following detailed description when taken in conjunction with the accompanying drawings, which are a part of this disclosure and which illustrate, by way of example, principles of the inventions disclosed.

DESCRIPTION OF THE FIGURES

The accompanying drawings facilitate an understanding of the various embodiments.

FIG. 7 is a section though the scroll assembly of FIGS. 4 and 5;

FIG. 8 is a detail sectional view of the hub of the scroll assembly of FIGS. 4 and 5;

FIG. 9 is an isometric view of the shaft portion of the scroll assembly of FIGS. 4 and 5;

FIG. 22 is a cut-away isometric view of a simple labyrinth alternative to the labyrinth of FIGS. 16 to 18;

FIG. 23 is a section of the labyrinth of FIG. 22;

FIG. 24 is an elevation of the labyrinth of FIG. 22;

DETAILED DESCRIPTION

Figure 1:
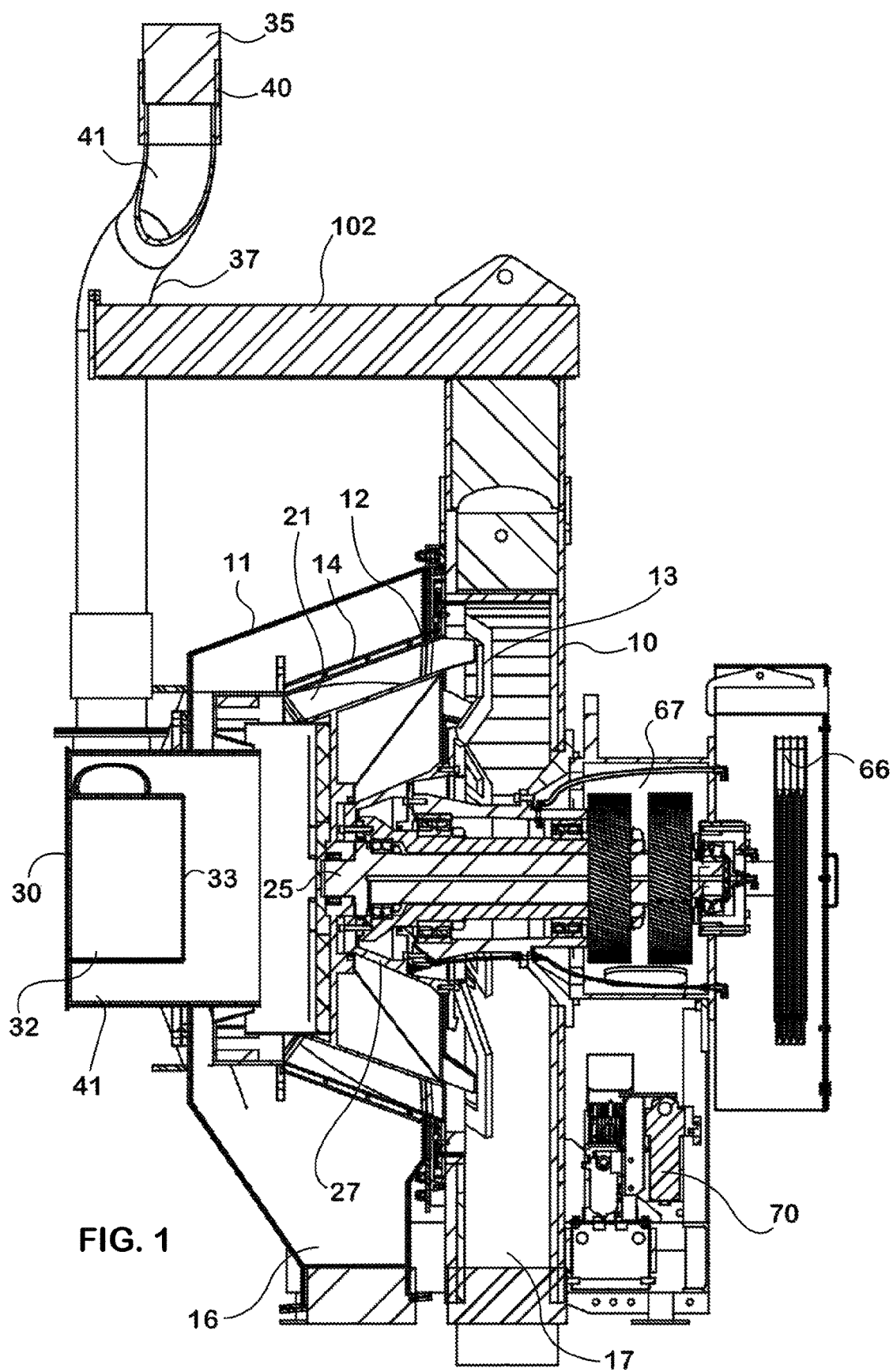
FIG. 1 is a vertical section through centrifugal screening apparatus in accordance with this disclosure.
Figure 2:
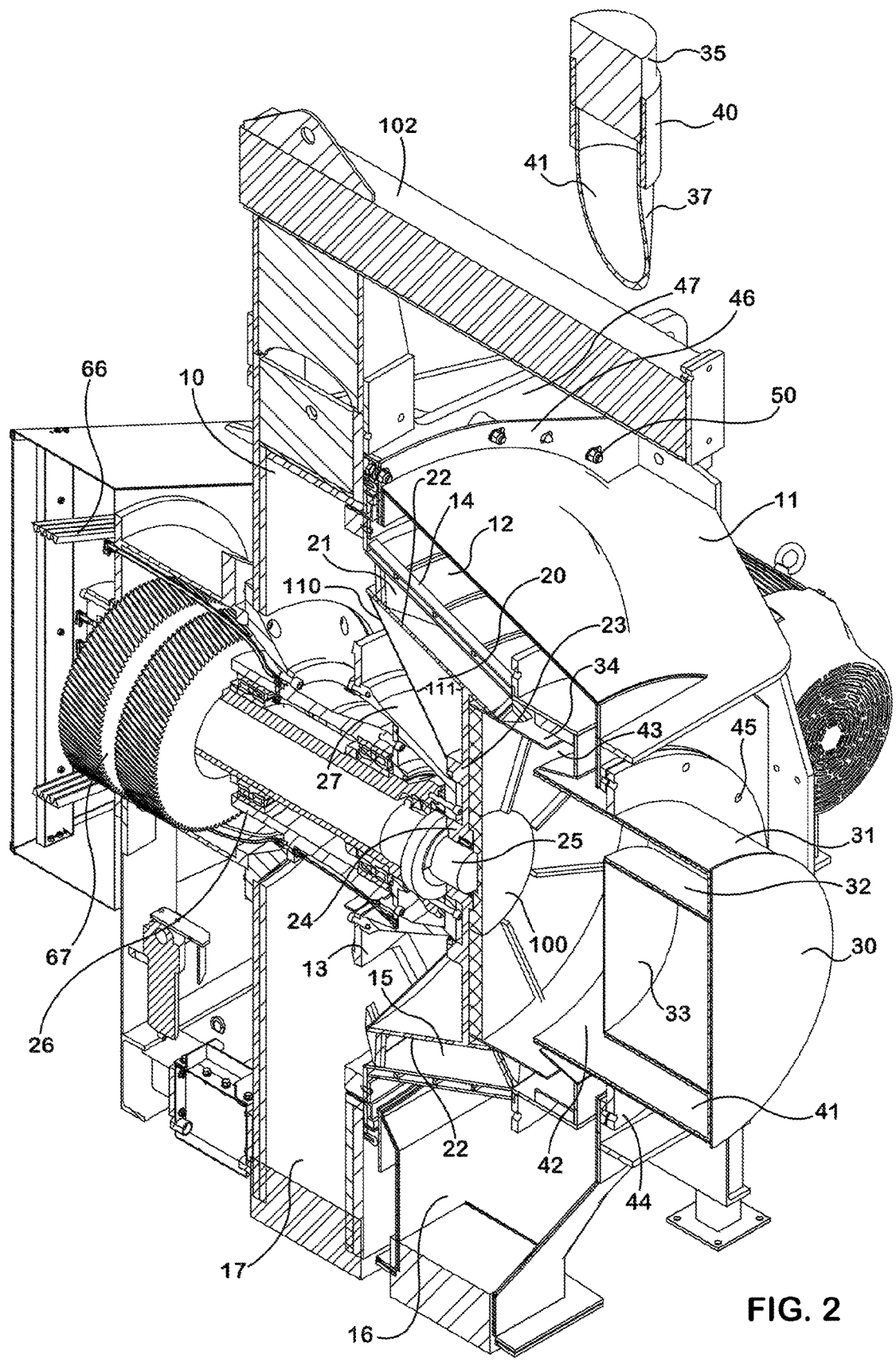
FIG. 2 is a cut-away isometric view of the apparatus of FIG. 1.
Figure 3:
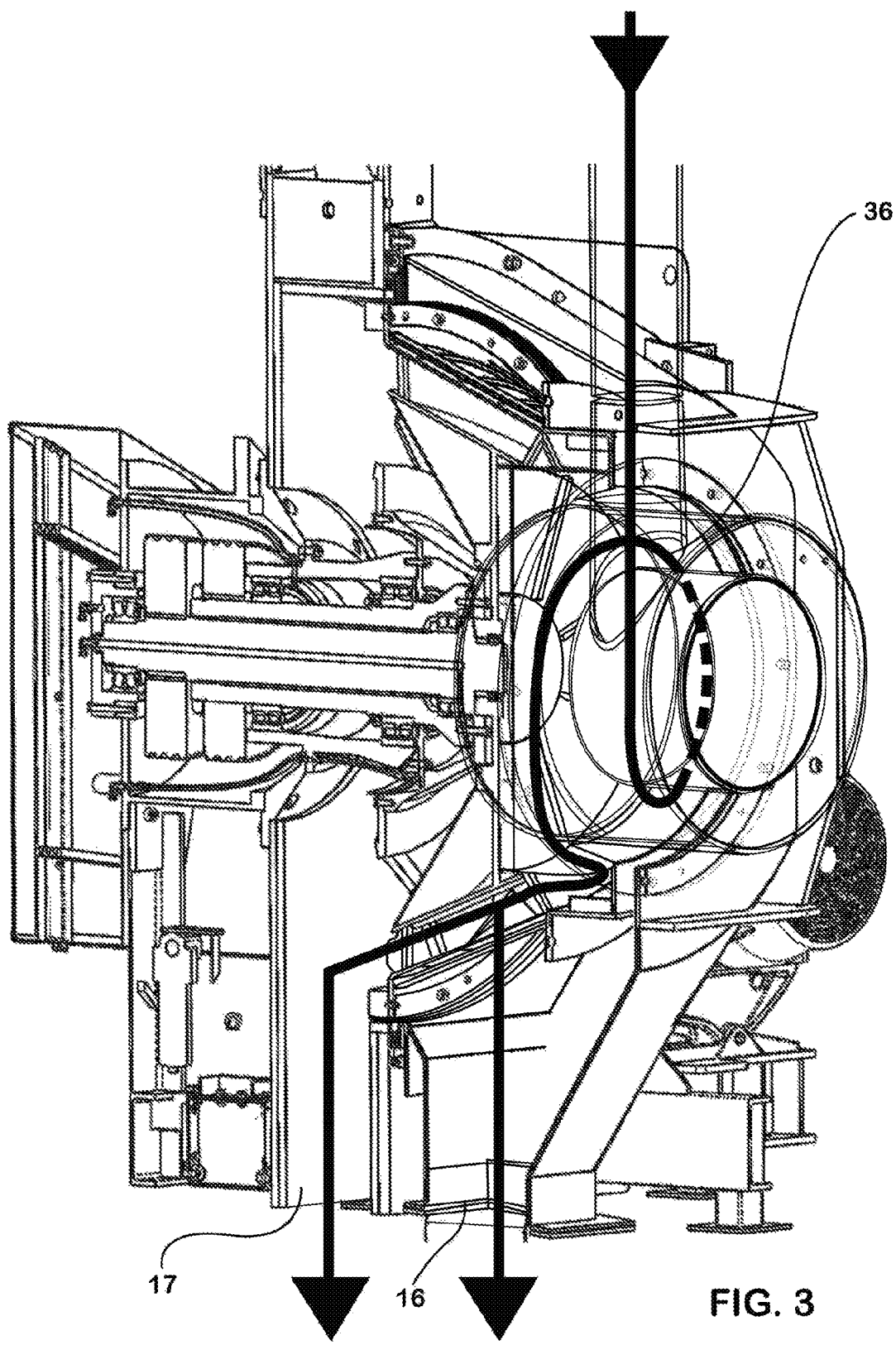
FIG. 3 is a cut-away, isometric wire frame view of the apparatus of FIG. 1, showing product and effluent flow paths therethrough.
Figures 4, 5:
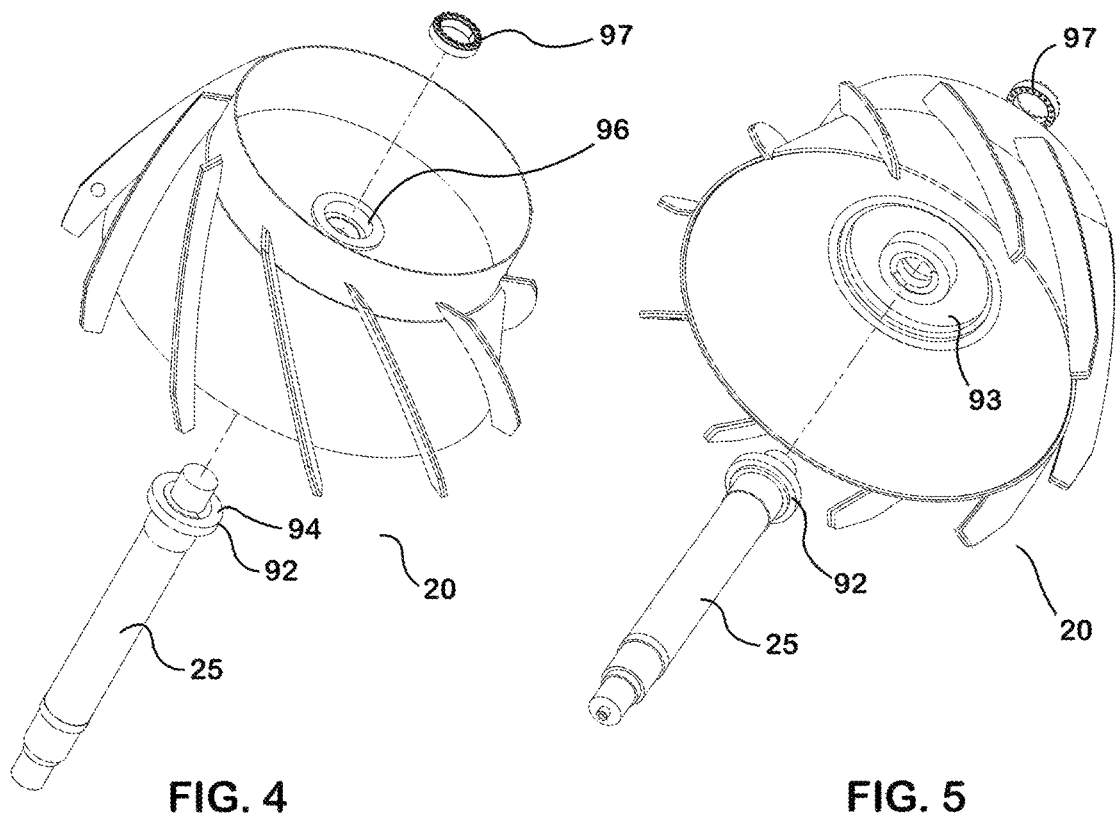
FIGS. 4 and 5 are exploded isometric views of a scroll assembly for use in the apparatus of FIG. 1.
Figure 6:
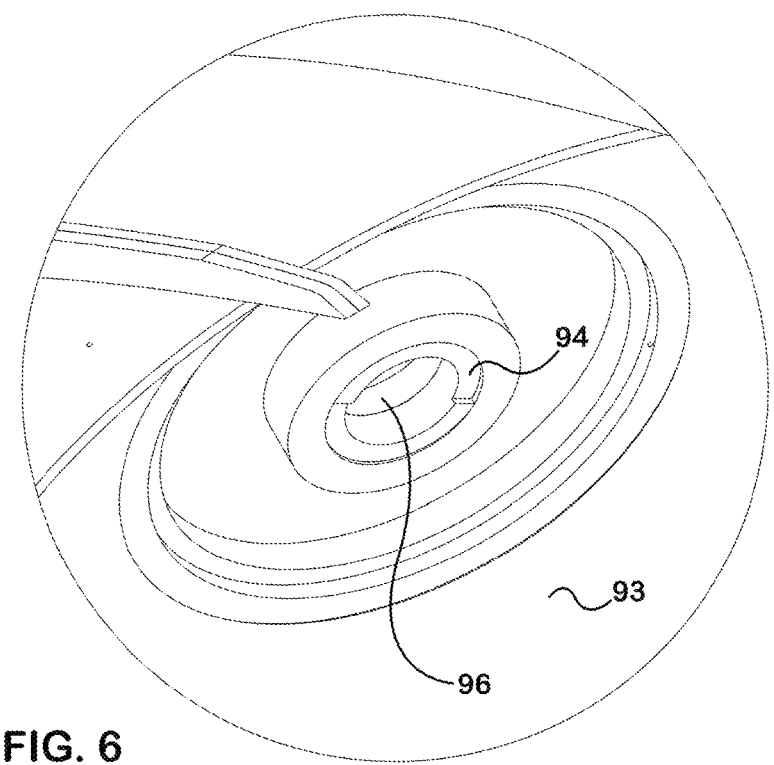
FIG. 6 is a detail view of the hub of the scroll member portion of FIGS. 4 and 5.

In the FIGS. 1 to 3 there is provided generally a centrifugal screening apparatus including an inner "dry side" housing portion 10 and an outer "wet side" housing portion 11. A screen assembly 12 is mounted for rotation in the wet side housing portion 11 and includes a base-of-spoke piece 13 and a frustoconical screen member 14 having a wedge-wire formed inner screening surface 15 and removably secured by its base to the base-of-spoke piece 13. The base of spoke piece 13 cooperates with the housing 10 to substantially divide the housing 10, the wet side housing portion 11 receiving filtrate passing through the screen member 14 to an effluent chamber 16 and the dry side housing portion 12 receiving product passing through the base-of-spoke piece 13 to a product delivery chamber 17. The filtrate or effluent chamber 16 is integrally formed with the outer wet side housing portion 11.

A scroll assembly 20 has a plurality of substantially helical scroll vanes 21 supported on a conical liner 22 fabricated to a drive plate 23. The drive plate 23 has a hub 24 secured to an inner drive shaft 25 whereby the scroll assembly 20 is mounted for rotation within the screen member 14 with an edge of each said vane 21 lying in selected proximity to the screening surface 15. The inner drive shaft 25 forms part of a drive assembly including an outer shaft 26 mounting the base-of-spoke piece 13 by a drive cone 27, the inner 25 and outer 26 drive shafts being differentially driven to rotate the screen assembly 12 and the scroll assembly 20 about the machine axis at different speeds in use.

An inlet assembly 30 is supported on the wet side housing portion 11 and includes an inlet body 31 defining a substantially annular inlet space 32 with an axial occluding plug portion 33, the annular inlet space 32 being substantially coaxial with and opening in to an open apical end 34 of the screen member 14. A material supply conduit 35 delivers the material to be screened under gravity head to the annular inlet space 32, the material supply conduit 35 being aligned in a tangent to the annular inlet space 32 to deliver said material to the screening surface 15 substantially in the direction of rotation of the screen assembly 12, as shown in the flow path 36 of FIG. 3.

The inlet body 31 includes an integral spigot 37 connected to the supply conduit 35 via sleeve coupling 40, permitting decoupling of the inlet assembly 30 from the supply conduit 35 for maintenance.

The annular inlet space 32 and spigot 37 are lined with a wear resistant tiles 41 formed of sintered alumina. The inlet body 31 is fabricated from steel. The wear resistant tiles 41 are bonded to the steel with epoxy based adhesive grouting composition.

The inlet assembly 30 is hinged to the wet side housing portion 11. The inlet assembly 30 extends an outer cylindrical wall portion 42 into the wet side housing portion 11 to confine the feed to an annular space 43 defined by the screening surface 15 and the scroll vanes 21. The hinge arrangement (not shown) hinging the inlet assembly 30 to the wet side housing portion 11 is positioned and configured to allow the inlet assembly 30, including the wall portion 42 extending into the housing portion 11, to clear the housing portion 11 to enable maintenance access. The inlet assembly 30 is sealed to the housing portion 11 by a gasketed flange 44 compressed to the housing portion 11 closure bolts installed through holes 45.

Figure 15:
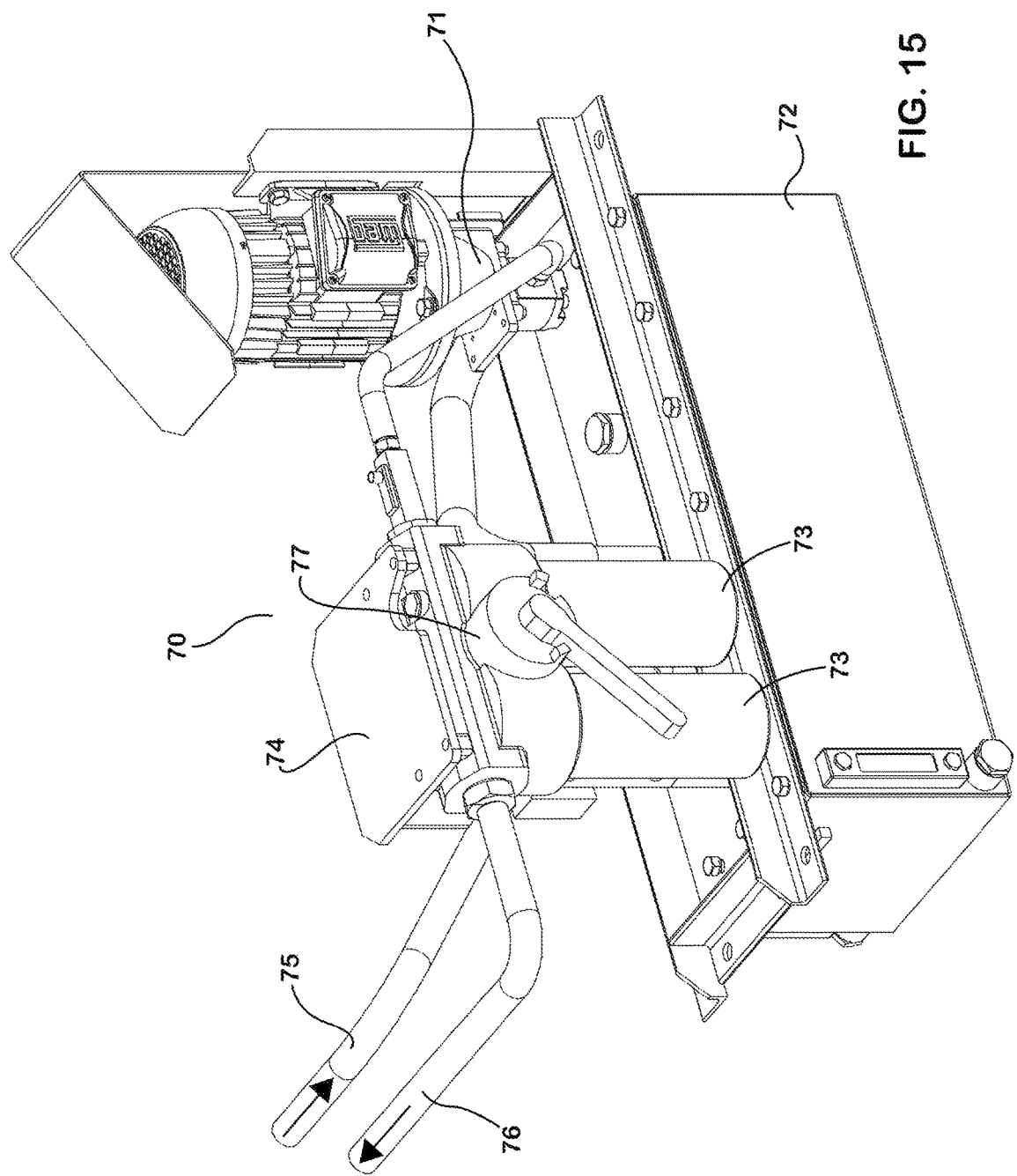
FIG. 15 is an isometric view of a gearbox lubrication system as used in the apparatus of FIG. 1.
Figure 16:
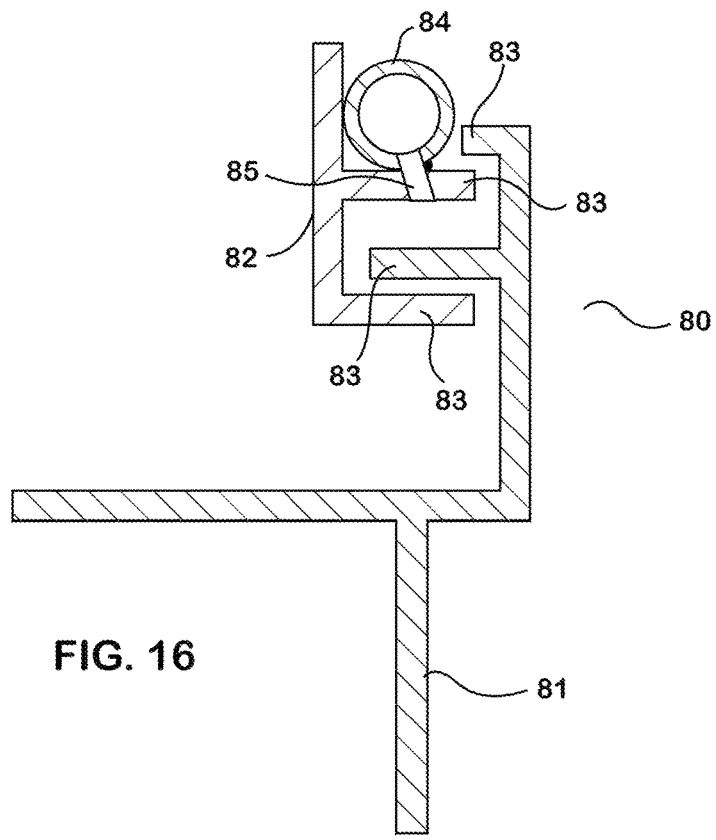
FIG. 16 is a section though components of a pressurized labyrinth for use in the apparatus of FIG. 1.

The fixed, inner portion dry side housing portion 10 is associated with and supports the drive means and the outer, wet side housing portion 11 associated with the inlet assembly 30 each have complementary peripheral mating flanges 46, 47 secured with selectively releasable fixing means 50 as detailed in FIGS. 15 and 16. The housing portions 10, 11 are selectively separable substantially in the plane of the join between the base-of-spoke piece 13 and the screen member 14.

The selectively releasable fixing means 50 includes a plurality of circumferentially spaced key slots 51 associated with the peripheral mating flange 46 of the inner dry side housing portion 10 and each supporting a blind stud 52, in this embodiment a stainless steel bolt. Corresponding stud holes 53 associated with the peripheral mating flange 47 of the outer, wet side housing portion 11 cooperate with nut 54 and washer 55 securing means selected to engage the studs 52 to clamp the peripheral mating flanges together.

The key slots 51 are formed in slot bodies 56 welded at 57 outward of a gasketed sealing flange portion 60 of the inner dry side housing portion 10, each slot body 56 and blind stud being retained in assembly by a polyurethane elastomer resilient retainer 61 adapted to pass over the stud 52 and substantially encapsulate the slot body 56. The welded slot bodies 56 are formed of stainless steel.

The resilient retainer 61 comprises a cap having a cylindrical side wall 62 adapted to engage the slot body 56 and substantially closed at one end by an end wall 63 having an aperture 64 adapted to pass over and engage the stud 52. The resilient retainer 61 may be threaded on both of the inner cylindrical side wall 62 to engage a complementary threaded side surface 65 of the slot body 56. The end wall aperture 64 is internally threaded to engage the corresponding threaded stud 52.

The housing portions 10, 11 are hinged together about a substantially vertical hinge (not shown) to provide access to the wet side components for ground-level maintenance. The hinge portions are geometrically selected to cooperate with the hinged inlet assembly 30 as described above to allow the assembly of the outer housing portion 11 and inlet assembly 30 to be opened with ample clearance of the wet-end parts, to provide maintenance access to the entire wet side of the apparatus. In the aggressive environment anticipated for screen machines, the hinge portion or portions are lubricated by a positive pressure lubricator (not shown), in this embodiment comprising a grease reservoir pressurized by a spring loaded piston and having a delivery outlet spigot screwed into the bore of each hinge to lubricate the pin-to-bore surfaces thereof.

The drive for the respective shafts 25, 26 includes a motor driven transmission belt 66 driving a power-dividing gearbox 67 providing the differential drive through the concentric shafts 25, 26. A pressurized-circulation lubrication system 70 as illustrated in detail in FIG. 15 includes a lubricant positive displacement impeller pump 71 delivering lubricant from a reservoir 72 to two disposable spin-on filter cartridges 73 mounted in parallel on a selector assembly 74. Circulated lubricant is returned to the reservoir 72 via a low pressure return line 75. The selector assembly 74 delivers lubricant oil to the gearbox 67 via a supply line 76.

The selector assembly 74 includes a manual, lever single action, filter selecting changeover valve 77 and respective non-return valves for each filter 73.

Figure 17:
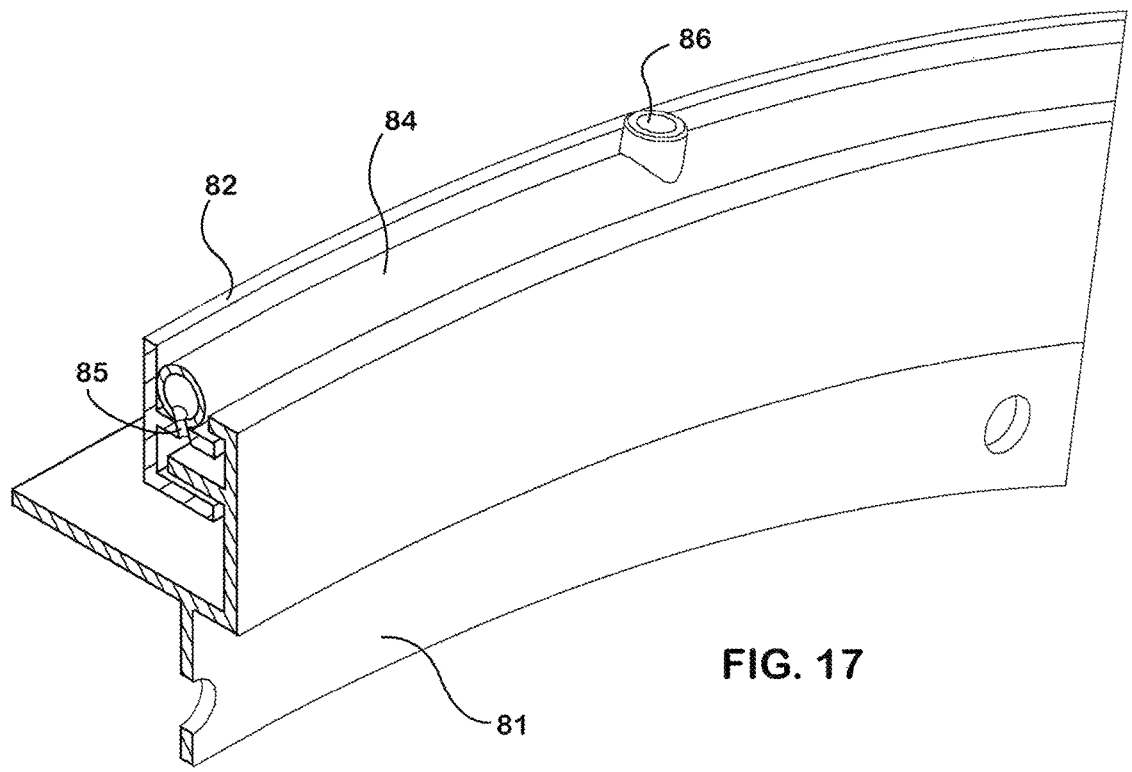
FIG. 17 is a cutaway isometric view of the labyrinth arrangement of FIG. 16.
Figure 18:
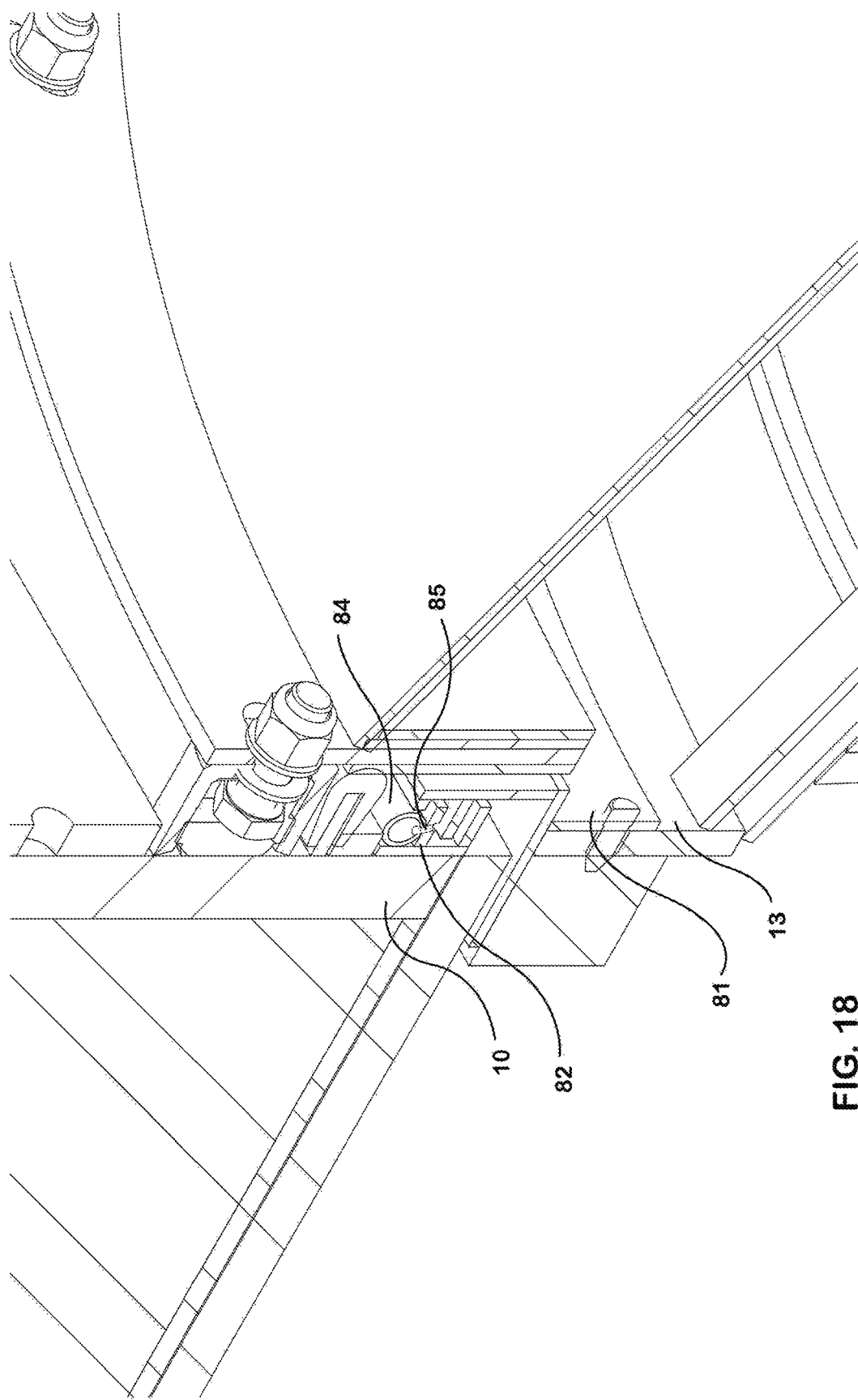
FIG. 18 is a cutaway isometric view of the labyrinth arrangement of FIG. 16 in the context of the apparatus of FIG. 1.
Figure 19:
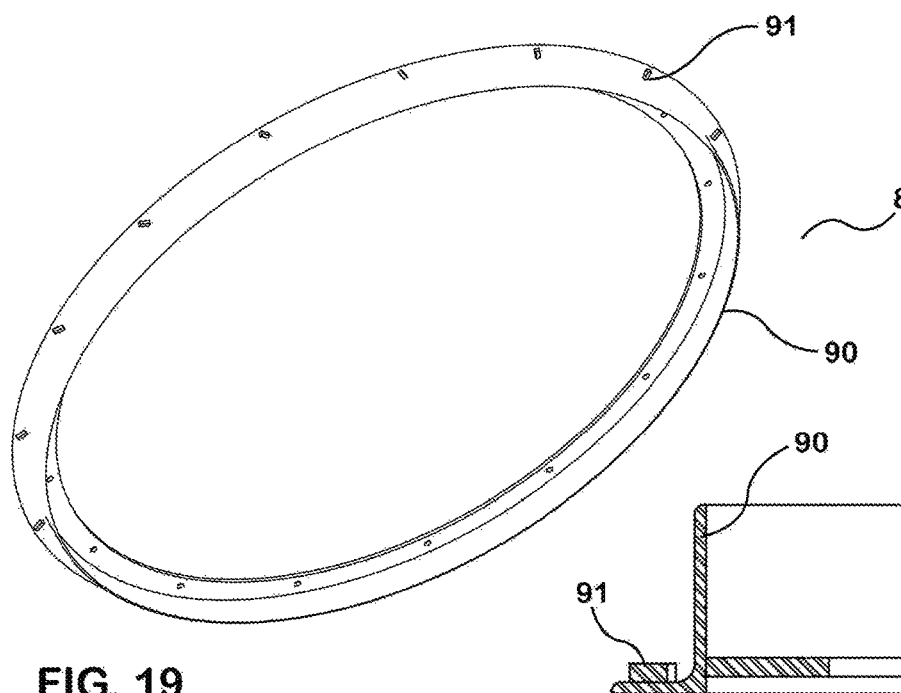
FIG. 19 is an isometric view of a slinger member as an alternative to a labyrinth and usable in apparatus of the type illustrated in FIG. 1.
Figure 20:
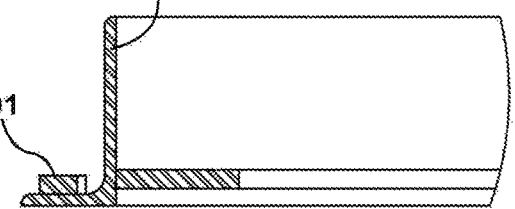
FIG. 20 is a section through the slinger member of FIG. 19.
Figure 21:
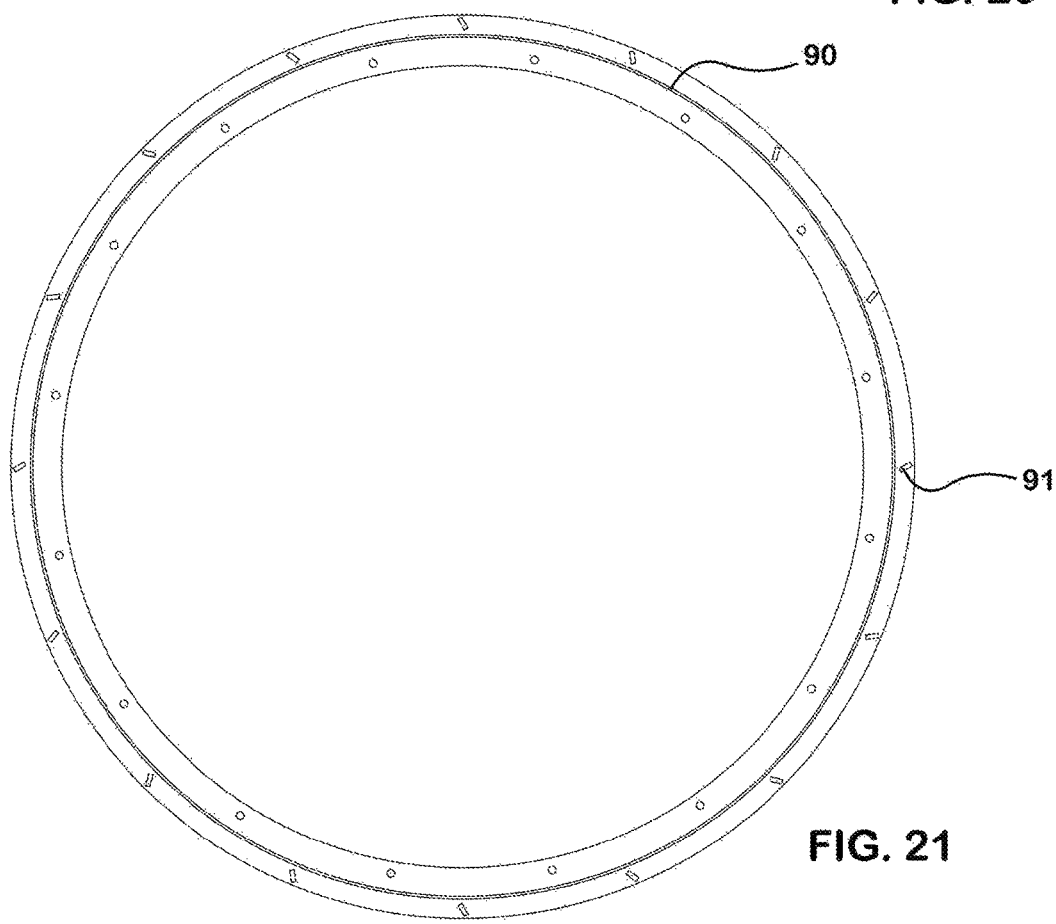
FIG. 21 is an elevation of the slinger member of FIG. 19.

Cross contamination of the product and effluent or filtrate streams in the embodiment of FIGS. 1 to 3 is specifically addressed in the detail of FIGS. 16 to 18 in a first embodiment, FIGS. 19 to 21 in a second embodiment and FIGS. 22 to 24 in a third embodiment of exclusionary methods.

In the embodiments of FIGS. 16 to 18, and 22 to 24 (where like components are numbered alike) the exclusionary principle is one of a labyrinth, wherein the rotating base of spoke piece 13 cooperates with the inner housing 10 via a labyrinth 80 selected to substantially resist filtrate contamination of the product. The labyrinth 80 include cooperating labyrinth members 81, 82 machine screwed to a respective one of the base of spoke piece 13 and a portion of the inner housing 10 surrounding its periphery. The passive labyrinth members 81, 82 of FIGS. 22 to 24 have two cooperating pairs of closely-running annular ridges 83 interleaved to create the labyrinth.

The labyrinth of FIGS. 16 to 18 is pressurized with air via a manifold 84 comprising an annular passage feeding a pressurized fluid into the labyrinth via a plurality of ports 85. The pressurized air supply 86 is not a contaminant for either of the product or effluent streams.

As an alternative embodiment to or in addition to a labyrinth, cross contamination may be addressed as per the embodiment of FIGS. 19 to 21 by the rotating base of spoke piece 13 cooperating with the static housing portion 10 by means of a slinger member 87 machine screwed to the base of spoke piece 13. The slinger member 87 includes an axially directed annular wall 90 and adapted to run in proximity to the aperture between the housing portions 10, 11 receiving filtrate (effluent) passing through the screen member 14 and product passing through the base-of-spoke piece 13 respectively, and a plurality of circumferentially spaced slinger vanes 91 inclined to the machine axis and located radially outward of and adjacent to the annular wall 90.

FIGS. 4 to 9 illustrate particular features of the scroll assembly 20 as embodied. As stated the drive means includes the concentric drive shaft portions including a scroll assembly drive shaft 25. The present embodiment includes an axial adjuster located at the mounting hub 24 to drive shaft 25 connection and operable to adjust the selected proximity of the scroll vanes 21 and the screen surface 15.

The axial adjuster includes a shaft portion 92 and a scroll portion 93 each having a respective camming surface 94 whereby relative rotation of the scroll portion 93 and the shaft portion 92 axially adjusts the selected proximity. The shaft 25 end portion 95 and the scroll hub 24 bore 96 are both plain and are adapted to be locked together by RINGFEDER® stepless locking means 97. The axial adjuster is protected in use by a polyurethane elastomer cap 100.

In use the hinged inlet assembly 30 and the housing outer portion 11 is swung away and the cap 100 removed, whereupon the axial adjuster is exposed. The RINGFEDER® stepless locking means 97 is released and the scroll member 20 is rotated on the shaft 25 to effect adjustment of the clearance between the scroll vanes 21 and the screening surface 15 of the screen member 14. Thereafter the locking means 97 may be engaged, the protection 10 installed and the housing portions closed together.

Figure 10:
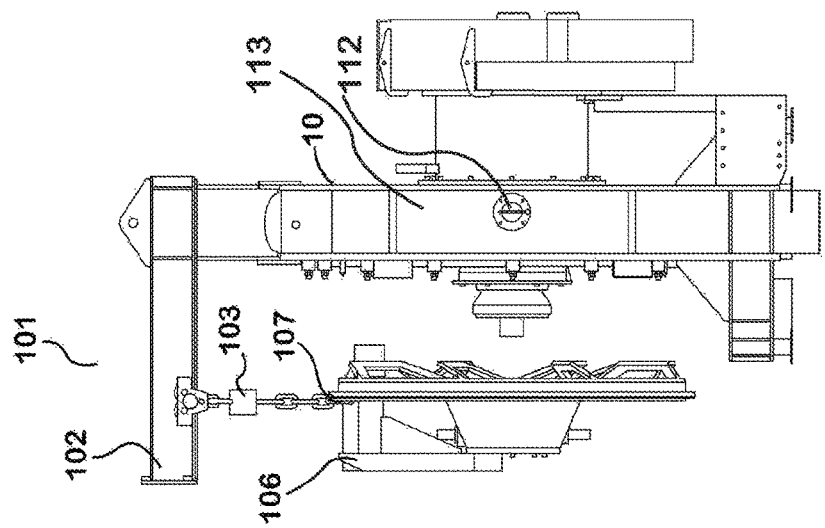
FIGS. 10 to 12 is a progression of side views showing maintenance disassembly of apparatus according to FIG. 1.
Figure 11:
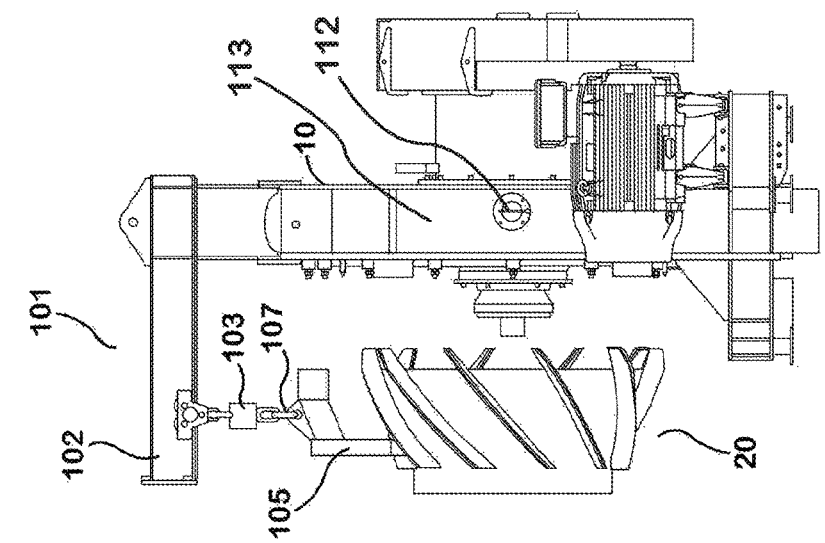
Figure 12:
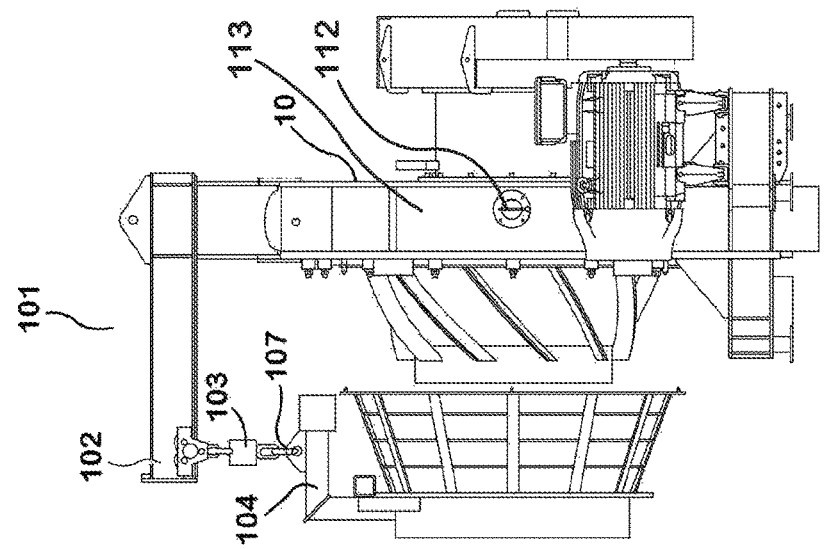
Figure 14:
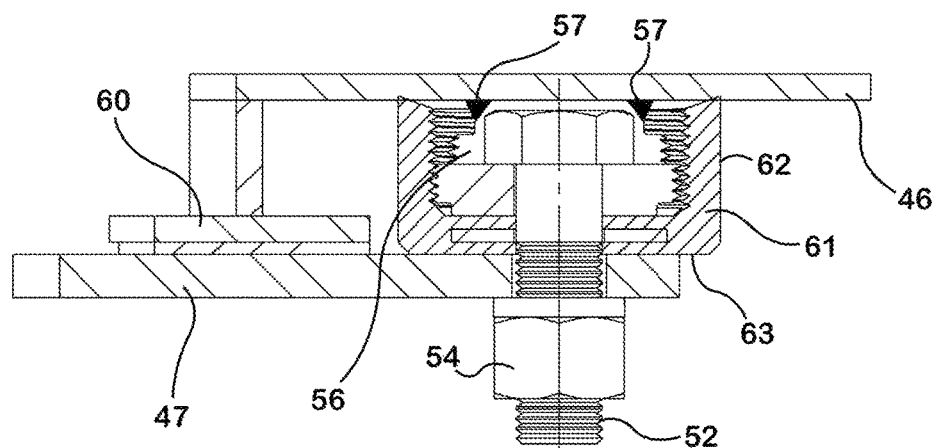
FIG. 14 is detail section of the securing means of FIG. 13.
Figure 13:
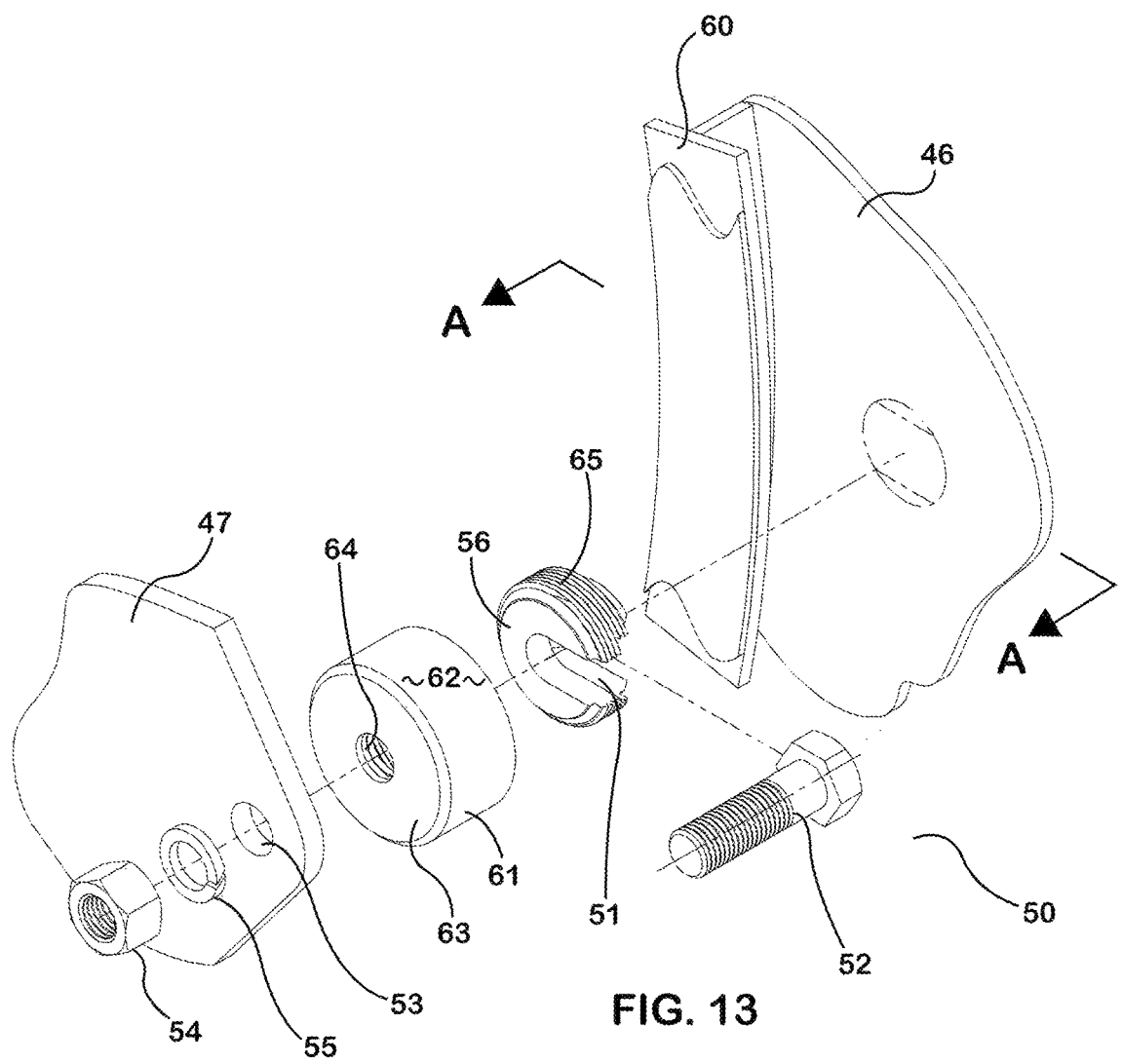
FIG. 13 is a detail isometric view of the securing means between housing portions of the apparatus of FIG. 1.

A hoist assembly 101 (best illustrated in FIGS. 10 to 12) includes a monorail 102 supported by the fixed inner housing portion 10 and extending overhead of the outer housing portion 11. A chain hoist 103 is mounted for movement along the monorail 102. Custom hoist adapters 104, 105 and 106 connect a lifting terminus 107 of the hoist 103 to the screen member 14, the scroll member 20 and the base-of-spoke piece 13 respectively. The respective hoist adapters 104, 105 and 106 are configured to lift the respective component 14, 20 and 13 substantially though its centre of gravity.

The scroll assembly 20 includes a substantially frustoconical liner 22 as described, substantially interconnecting the inner edges of the vanes 21 and spaced from the screening surface 15, the liner extending substantially to the base-of-spoke piece 13 and to the outer ends of the vanes 21.

The liner 22 is integrated into the collar portion 34 that cooperates with the inlet assembly 30 to confine the infeed of material to the annulus 43 containing the vanes 21. The conical included angle of the liner 22 is such that product hang-up may occurs. An inner conical wall portion 110 creates an enclosed annulus 111 within the liner 22 and presenting a flatter conical included angle. By this means any material passing into the space is discouraged from hanging up since the centrifugal component of the forces acting through the flatter conical surface will direct the product toward the base-of-spoke piece 13.

Figures 25, 26:
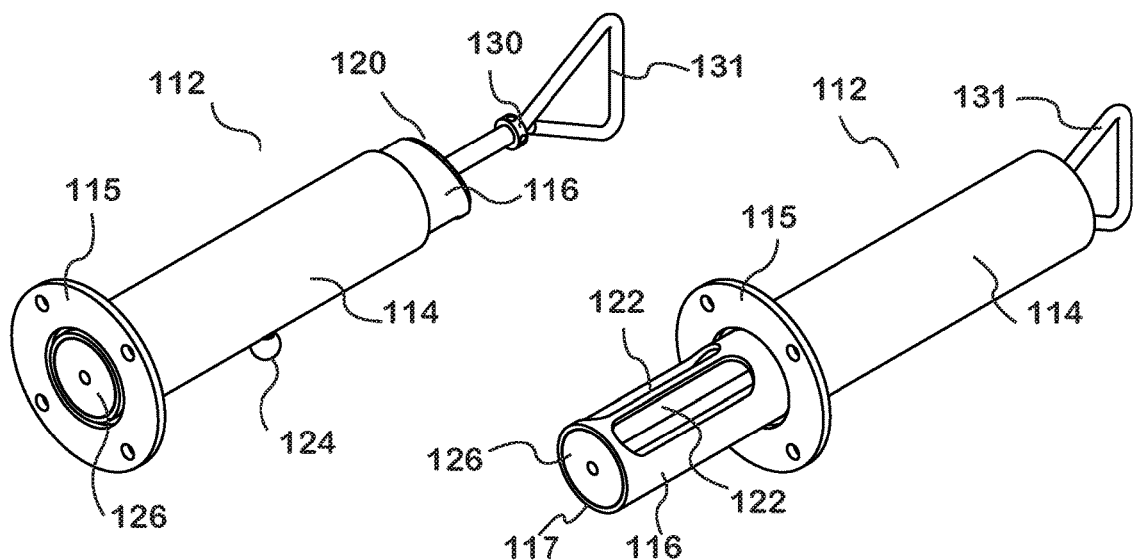
FIG. 25 is an isometric view of a sampler for use with the apparatus of FIG. 1, operatively closed.
FIG. 26 is an isometric view of the sampler of FIG. 25, operatively open.
Figure 27:
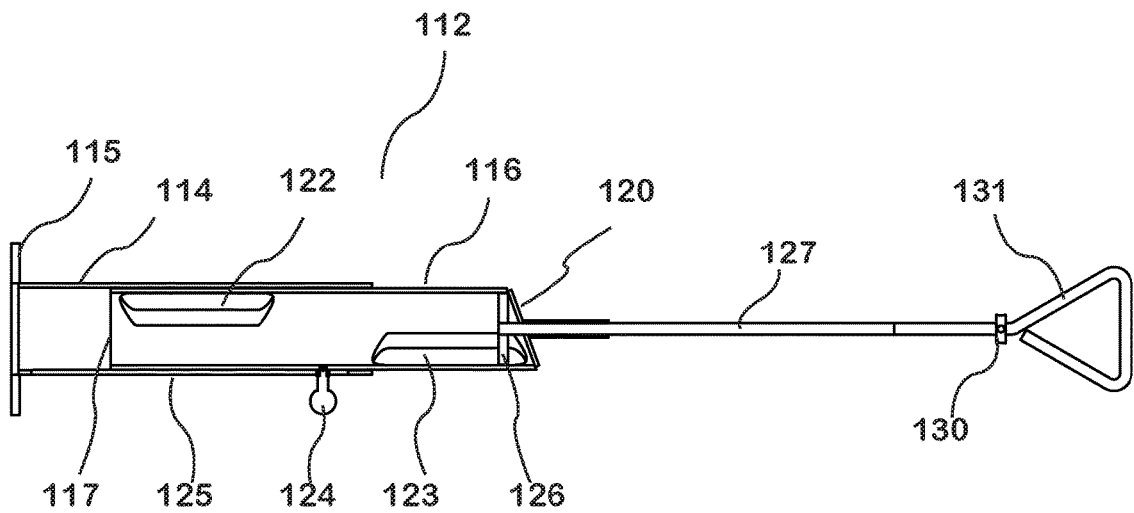
FIG. 27 is a longitudinal section of the sampler of FIGS. 25 and 26, operatively discharged.

A product sampler assembly 112 is located at an aperture in a side wall 113 of the product delivery chamber 17, and is illustrated in detail in FIGS. 25 to 27. The product sampler 112 comprises a cylindrical body 114 mounted to the side wall 113 by a flange 115. The cylindrical body 114 has its cylindrical axis substantially perpendicular to a product flow in product delivery chamber 17.

A cylindrical sample shuttle 116 has an open inner end 117 and a substantially closed outer end 120 including an integral rod guide 121. The cylindrical sample shuttle 116 has a pair of inner sampling cut outs 122 which are facing generally upward into the product flow in the product chamber 17 in use. A sample delivery cut out 123 faces generally downward in use to gravitationally aid sample recovery from the sampler 112 in use.

A piston 126 is secured to a rod 127 passing through the rod guide 121 and is made captive by a locking collar 130 adjacent a push/pull handle 131. The piston 126 is movable in the shuttle 116 between the position illustrated in FIGS. 25 and 26 and the position as illustrated in FIG. 27.

The sample shuttle 116 is made captively movable in the cylindrical body 114 between a sampling position (as in FIG. 26) and a sample delivery position (as in FIG. 27) by an operating handle 124 attached to the sample shuttle 116 and extending out of and movable along an axial slot 125 formed in the cylindrical body 114.

In use, in normal, non-sampling operation of the centrifuge (FIG. 25), the piston 126 is advanced in the shuttle 116 and the shuttle 116 is withdrawn by the operating handle 124 until the face of the piston 126 and the open inner end 117 are essentially flush with the flange 115. To sample, as in FIG. 26, the operating handle 124 is used to insert the open outer end 117 (occluded by the piston 126) into the product chamber 17, exposing the inner sampling cut outs 122 to the flow of product in the product chamber and filling the shuttle 116 with sample. The filled shuttle 116 is then withdrawn with handle 124.

Thereafter withdrawal of the push/pull handle 131 draws the rod 127 and piston 126 assembly to discharge the sample through the cutout 123 into a collection cup (not shown).

Apparatus according to the embodiment has specific advantages over prior art scroll centrifuge machines in that the material supply conduit being aligned in a tangent to the annular space rotates the incoming material substantially in the direction of rotation of the screen assembly. The material needs less acceleration by the screen to reach centrifugally effective speeds, increasing throughput and reducing screen wear. The annular space effectively confines the feed to adjacent the screen surface. The apparatus does not require velocity arrestors or the like.

The use of a horizontal machine with an inlet assembly according to the above does not suffer from the disadvantage of the few prior art horizontal machines of the feed extending the floor plan, since the feed in the present apparatus is tangential to the inlet and machine axis.

The housing portions 10, 11 being selectively separable substantially in the plane of the join between the base-of-spoke piece 13 and the screen member 14 means that the join is accessible for maintenance when the housing portions are separated.

The blind stud 52 being retained by the polyurethane cap 61 to the housing inner portion 10 by means that the arrangement is protected from the aggressive erosive and corrosive environment. This provides an inexpensive and easily replaceable fixing system that addresses both wear and corrosion problems of alternative fixing methods.

The respective labyrinth portions members are a replaceable service item which operates in a high-wear region and additionally serves to protect that portion of the base-of-spoke piece in a sacrificial manner.

The slinger member is a replaceable service item which operates in a high-wear region, and additionally serves to protect that portion of the base-of-spoke piece in a sacrificial manner.

The axial adjuster according the embodiment allows adjustment substantially without disassembly. Initial condition need not be measured at all; the adjustment is dynamic in that the parts are in situ while the adjustment is made. The adjustment can be measured in real time or the clearance fully closed up by one direction of relative rotation of the scroll on the shaft rotation and backed off to create a selected working clearance.

Whereas the prior art requires an external crane, certain embodiments herein are capable of change out of components without additional overhead lifting gear. Whereas prior art overhead lifting gear is generally multipurpose and must be rated accordingly, the present embodiments are rating matched to the actual machine components. The relative short cable or chain length to the component reduces the risk of load swing.

In the foregoing description of certain embodiments, specific terminology has been resorted to for the sake of clarity. However, the disclosure is not intended to be limited to the specific terms so selected, and it is to be understood that each specific term includes other technical equivalents which operate in a similar manner to accomplish a similar technical purpose. Terms such as "left" and right", "front" and "rear", "above" and "below" and the like are used as words of convenience to provide reference points and are not to be construed as limiting terms.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

In addition, the foregoing describes only some embodiments of the invention(s), and alterations, modifications, additions and/or changes can be made thereto without departing from the scope and spirit of the disclosed embodiments, the embodiments being illustrative and not restrictive.

Furthermore, invention(s) have described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention(s). Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment.

What is claimed is:

1. Centrifugal screening apparatus including:
   a housing;
   a screen assembly mounted for rotation in said housing and including a base-of-spoke piece and a substantially frustoconical screen member having an inner screening surface and removably secured by its base to the base-of-spoke piece, the base of spoke piece cooperating with the housing to substantially divide the housing into housing portions receiving filtrate passing through the screen member and product passing through the base-of-spoke piece respectively;
   a scroll assembly having a plurality of substantially helical scroll vanes and mounted for rotation within said screen member with an edge of each said vane lying in selected proximity to said screening surface;
   drive means selected to differentially drive the rotation of said screen assembly and said scroll assembly about a machine axis; and
   an inlet assembly supported on said housing and including an inlet body defining a substantially annular inlet space substantially coaxial with and opening in to an open apical end of said screen member and a material supply conduit delivering said material to be screened to said annular space, said material supply conduit being aligned in a tangent to said annular space selected to deliver said material to said screening surface substantially in the direction of rotation of the screen assembly.

2. Centrifugal screening apparatus according to claim 1, wherein said inlet assembly includes an inlet body forming said annular inlet space and including an integral spigot to said supply conduit, said inlet space and spigot being lined with a wear resistant material.

3. Centrifugal screening apparatus according to claim 2, wherein the inlet body is selected from fabricated or cast metal, moulded engineering polymer and composites.

4. Centrifugal screening apparatus according to claim 2, wherein said wear resistant lining is selected from wear resistant elements bonded into the inlet body to form the lining and a wear resistant ceramic liner about which the inlet body is formed.

5. Centrifugal screening apparatus according to claim 4, wherein the wear resistant elements are sintered ceramic tiles.

6. Centrifugal screening apparatus according to claim 4, wherein said wear resistant lining is an integral hot sintered ceramic liner having a spigot portion merging with a substantially involute annular inlet space portion.

7. Centrifugal screening apparatus according to claim 1, wherein the axis of the tangential material supply conduit lies in a plane that intersects the machine axis by an angle of from 0° to about 10° from the perpendicular, measured away from the screen assembly.

8. Centrifugal screening apparatus according to claim 1, wherein the material supply conduit delivering said material to be screened to said annular space delivers the material to a pump.

9. Centrifugal screening apparatus according to claim 8, wherein said machine axis is horizontal.

10. Centrifugal screening apparatus according to claim 1, wherein said housing portions include a fixed inner portion associated with said drive means and a moveable outer portion associated with said inlet assembly, said inner and outer portions having complementary peripheral mating flanges secured with selectively releasable fixing means.

11. Centrifugal screening apparatus according to claim 10, wherein said housing portions are selectively separable substantially in the plane of ajoin between the base-of-spoke piece and the screen member.

12. Centrifugal screening apparatus according to claim 10, wherein said selectively releasable fixing means includes a plurality of circumferentially spaced key slots associated with the peripheral mating flange of said inner portion and each supporting a blind stud, corresponding stud holes associated with the peripheral mating flange of said outer portion, and securing means selected to engage said studs to clamp said peripheral mating flanges together.

13. Centrifugal screening apparatus according to claim 12, wherein said key slots are formed in slot bodies welded outward of the peripheral mating flange of said inner portion, each said slot body and blind stud being retained in assembly by a resilient retainer adapted to pass over said stud and encapsulate said slot body.

14. Centrifugal screening apparatus according to claim 12, wherein said blind stud includes a bolt and said securing means includes a nut.

15. Centrifugal screening apparatus according to claim 10, wherein said housing portions are relatively conjoined by one or more hinge portions.

16. Centrifugal screening apparatus according to claim 15, further comprising a positive pressure lubricator, wherein said one or more hinge portion is lubricated by the positive pressure lubricator.

17. Centrifugal screening apparatus according to claim 10, wherein said fixed inner portion supports a hoist assembly selected to enable maintenance removal and replacement of one or more of said scroll assembly and said screen assembly.

18. Centrifugal screening apparatus according to claim 1, wherein at least the housing portion receiving filtrate passing through the screen member is formed of moulded polymer or polymer composite.

19. Centrifugal screening apparatus according to claim 1, wherein said drive means includes a motor and a power-dividing gearbox providing said differential drive through concentric shafts, said gearbox having a pressurized-circulation lubrication system including at least one lubricant pump delivering lubricant from a reservoir and at least two filters in parallel, each being associated with isolation valve means selected to allow filter maintenance without shutdown of said gearbox.

20. Centrifugal screening apparatus according to claim 19, wherein each said filter is a disposable spin-on filter cartridge.

21. Centrifugal screening apparatus according to claim 19, further comprising:
an inlet line from said pump and having a filter-selecting Y-valve, wherein said filters are supplied by the inlet line from said pump; and
each filter having a respective non-return valve on its delivery line.

22. Centrifugal screening apparatus according to claim 1, wherein the rotating base of spoke piece cooperates with the static housing via a labyrinth selected to substantially resist filtrate contamination of said product.

23. Centrifugal screening apparatus according to claim 22, further comprising a manifold associated with said housing, wherein said labyrinth is pressurized via the manifold associated with said housing.

24. Centrifugal screening apparatus according to claim 1, wherein the rotating base of spoke piece cooperates with the static housing by means of a slinger portion associated with said base of spoke piece and selected to substantially resist filtrate contamination of said product.

25. Centrifugal screening apparatus according to claim 24, wherein the slinger portion includes an axially directed annular wall secured to said base of spoke piece and adapted to run in proximity to an aperture between the housing portions receiving filtrate passing through the screen member and product passing through the base-of-spoke piece respectively, and a plurality of circumferentially spaced slinger vanes inclined to the machine axis and located radially outward of and adjacent to said annular wall.

26. Centrifugal screening apparatus according to claim 24, wherein the slinger portion includes a slinger member including said annular wall and said slinger vanes formed on a mounting flange adapted to be secured to said base of spoke piece.

27. Centrifugal screening apparatus according to claim 1, wherein the drive means includes respective concentric drive shaft portions extending axially substantially through said screen assembly, the scroll assembly drive shaft being connected to the scroll assembly by an axial adjuster operable to adjust said selected proximity.

28. Centrifugal screening apparatus according to claim 27, wherein said axial adjuster includes a shaft portion and a scroll portion each having a respective camming surface whereby relative rotation of said scroll portion and said shaft portion axially adjusts said selected proximity, and locking means selectively operable to rotationally secure said scroll portion and said shaft portion.

29. Centrifugal screening apparatus according to claim 28, wherein said locking means includes a ringfeder locking means.

30. Centrifugal screening apparatus according to claim 28, wherein one or both of said shaft portion and said scroll portion includes a replaceable service part.

31. Centrifugal screening apparatus according to claim 17, wherein said machine axis is substantially horizontal and said hoist assembly includes a rail supported by said fixed inner portion and extending overhead of said outer portion, a hoist mounted for movement along said rail, and hoist adapters connecting a lifting terminus of said hoist to one or more of said scroll assembly and said screen assembly.

32. Centrifugal screening apparatus according to claim 1, wherein the scroll assembly includes a substantially frusto-conical liner substantially interconnecting inner edges of said vanes and spaced from said screening surface, said liner extending substantially to said base-of-spoke piece.

33. A centrifugal screening apparatus according to claim 1, wherein metal faces of the scroll vanes are laminated with adhesively bonded ceramic elements.

34. A centrifugal scroll screen machine according to claim 1, wherein the housing portion receiving product passing through the base-of-spoke piece includes a product sampler comprising: a tubular body mounted by a first open end to a corresponding aperture though a wall of said housing portion, said tubular body having its tubular axis substantially perpendicular to a product flow in said housing portion; a sample shuttle comprising a tubular receptacle selectively and captively movable in said tubular body between a sampling position where a sampling portion extends into said product flow and a sample delivery position with a delivery portion extended out of a second open end of said tubular body, said sampling portion having side wall opening which faces substantially upstream of the product flow and said delivery portion having a delivery opening; and a piston assembly captively slidable in said sample shuttle and having a piston portion and a control rod portion extending out of said second open end, the rod portion being operable to selectively move said piston portion from a position located adjacent a terminal end of said sampling portion to a position adjacent an outer end of said delivery opening.

35. A centrifugal screening apparatus according to claim 34, wherein said tubular body and sample shuttle are each substantially cylindrical in section.

36. A centrifugal screening apparatus according to claim 34, wherein said sample shuttle is made captively moveable in said tubular body by an operating handle attached to said sample shuttle extending out of and movable along an axial slot formed in the cylindrical side wall portion of said tubular body.

* * * * *